(12) United States Patent
Steinmetz et al.

(10) Patent No.: US 9,351,635 B2
(45) Date of Patent: May 31, 2016

(54) ASSEMBLY AND METHOD FOR THE AUTOMATIC ROUGH POSITIONING OF OPHTHALMOLOGICAL EQUIPMENT

(75) Inventors: Dietmar Steinmetz, Bucha (DE); Michael Güntzschel, Jena (DE); Rico Fuchs, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 295 days.

(21) Appl. No.: 13/883,228

(22) PCT Filed: Nov. 3, 2011

(86) PCT No.: PCT/EP2011/005540
§ 371 (c)(1),
(2), (4) Date: Jul. 10, 2013

(87) PCT Pub. No.: WO2012/059227
PCT Pub. Date: May 10, 2012

(65) Prior Publication Data
US 2013/0286353 A1      Oct. 31, 2013

(30) Foreign Application Priority Data

Nov. 6, 2010    (DE) .......................... 10 2010 050 695

(51) Int. Cl.
*A61B 3/14*      (2006.01)
*A61B 3/00*      (2006.01)
(Continued)

(52) U.S. Cl.
CPC .............. *A61B 3/0083* (2013.01); *A61B 3/152* (2013.01); *G06K 9/00912* (2013.01); *G06K 9/00919* (2013.01); *G06T 7/0012* (2013.01)

(58) Field of Classification Search
CPC .... A61B 5/1077; A61B 5/7264; A61B 6/102; A61B 5/0064; A61B 5/0086; A61B 3/15; A61B 3/152; A61B 3/0083; A61B 2019/5214; A61B 19/5244; A61B 6/08; G06F 19/321; G06T 7/0012; A61F 2009/00846; G06K 9/00214; G06K 9/00912; G06K 9/00919

USPC .............. 378/205; 382/154; 606/4; 701/301; 351/205, 206, 208, 209, 245, 246
See application file for complete search history.

(56) References Cited

U.S. PATENT DOCUMENTS 4,139,280 A    2/1979    Kohler
5,568,208 A    10/1996   Van de Velde
(Continued)

FOREIGN PATENT DOCUMENTS

DE    198 16 486 A1    11/1999
DE    100 29 153 A1    12/2001
(Continued)

OTHER PUBLICATIONS

Joerg, L. Loehrer, F. Machine Translation of DE10029153. Obtained from the European Patent Office Mar. 22, 2015.*
(Continued)

*Primary Examiner* — Bumsuk Won
*Assistant Examiner* — Collin X Beatty
(74) *Attorney, Agent, or Firm* — Patterson Thuente Pedersen, IP (57) ABSTRACT

A solution for the individual automatic rough positioning of ophthalmological equipment with respect to ensure the diagnostic or therapeutic treatment of the patient. The assembly includes a positioning aid and a control unit for the automatic alignment of the axis of vision of the eye with the optical axis of the ophthalmological equipment. The positioning aid includes a chin rest and a forehead support which have corresponding controllable actuating devices. The assembly has an additional measuring device for recording the geometry of the face of the patient.

19 Claims, 4 Drawing Sheets

(51) Int. Cl.
*A61B 3/15* (2006.01)
*G06K 9/00* (2006.01)
*G06T 7/00* (2006.01)

(56) References Cited

U.S. PATENT DOCUMENTS

| | | | |
|---|---|---|---|
| 6,309,068 B1 | 10/2001 | Kohayakawa | |
| 7,401,921 B2 | 7/2008 | Baker | |
| 7,792,249 B2 | 9/2010 | Gertner | |
| 8,292,432 B2* | 10/2012 | Bischoff | A61B 3/14 351/206 |
| 8,331,635 B2* | 12/2012 | Hilbelink | G06T 7/0012 382/128 |
| 2003/0123026 A1* | 7/2003 | Abitbol et al. | 351/204 |
| 2007/0070294 A1* | 3/2007 | Kim | 351/206 |
| 2007/0183567 A1* | 8/2007 | Rotondo et al. | 378/38 |
| 2008/0243107 A1* | 10/2008 | Muhlhoff et al. | 606/4 |
| 2009/0132636 A1* | 5/2009 | Natanzon et al. | 709/201 |
| 2009/0161827 A1* | 6/2009 | Gertner | A61F 9/008 378/65 |
| 2010/0166294 A1* | 7/2010 | Marrion et al. | 382/154 |
| 2010/0172567 A1* | 7/2010 | Prokoski | A61B 5/0064 382/132 |
| 2011/0206274 A1* | 8/2011 | Tateno et al. | 382/154 |
| 2011/0224904 A1* | 9/2011 | Feiten et al. | 701/301 |

FOREIGN PATENT DOCUMENTS

| | | |
|---|---|---|
| DE | 102 50 569 A1 | 5/2004 |
| DE | 102 50 570 A1 | 5/2004 |
| EP | 2 116 179 A1 | 11/2009 |
| JP | 2002 034973 A | 2/2002 |
| WO | WO 98/22016 A2 | 5/1998 |

OTHER PUBLICATIONS

Niclass, Cristiano et al., "A CMOS 3D Camera with Millimetric Depth Resolution"; *Swiss Federal Institute of Technology*, Lausanne, Switzerland; AQUA-CONF 2004-001.

Smith, W.A.P. et al., "Face Recognition using Shape-from-shading"; Dept. of Computer Science, University of York; BMVC (13th British Machine Vision Conference) 2002; pp. 597-606.

Wagner, Holger et al., "3D measurement of human face by stereophotogrammetry"; Institute of Applied Optics, Friedrich-Schiller-University, Jena; DGaO Proceedings 2005, ISSN: 1614-8436.

* cited by examiner

ASSEMBLY AND METHOD FOR THE AUTOMATIC ROUGH POSITIONING OF OPHTHALMOLOGICAL EQUIPMENT

RELATED APPLICATIONS

The present application is a National Phase entry of PCT Application No. PCT/EP2011/005540, filed Nov. 3, 2011, which claims priority from DE Application No. 10 2010 050 695.8, filed Nov. 6, 2010, which applications are hereby incorporated by reference herein in their entirety.

FIELD OF THE INVENTION

The present invention relates to an approach for the individual automatic rough positioning of ophthalmological devices on a patient to be able to ensure the diagnostic or therapeutic treatment of the patient.

BACKGROUND OF THE INVENTION

Many ophthalmological devices nowadays have approaches for largely automatic alignment of the visual axis of the eye with the optical axis of the ophthalmological device. For the automatic alignment, numerous approaches are known from the prior art in which the two axes are usually adjusted with respect to one another automatically.

For example, DE 102 50 569 A1 describes an approach for positioning a device in x, y, and/or z coordinates with respect to an eye of a patient to be examined. In the ophthalmological device, the eye tracker unit, which has at least two different, adjustable magnifications is used for this purpose. The signal of the eye tracker unit is used not only for tracking a measuring mark and/or grid structure projected onto the eye, but also for detecting the position of the eye of the patient with respect to the optical axis of the ophthalmological device. Based on the determined position of the eye of the patient, appropriate control signals for positioning drives are then generated.

Another approach for positioning an ophthalmological device with respect to an eye of a patient to be examined is described in DE 102 50 570 A1. In this approach, however, the signals of an image recording unit, which for this purpose has an additional wide-angle setting, are used for the positioning. Here as well, a setpoint value concerning the magnitude and direction for the positioning device is generated and supplied to a positioning unit.

U.S. Pat. No. 7,401,921 B2 describes an automatic, motor-driven patient positioning aid for an ophthalmological measuring device. The motorized patient head support is likewise composed of a chin rest and a forehead support, of which there are two of each for orientation to the right or the left eye, and a corresponding motor assembly to allow movement of the head in three directions (X, Y, Z).

However, all three approaches require that for this automatic alignment process, the eye of the patient must have been brought into a fixed position using the chin rest and forehead support that are present; i.e., a rough adjustment of the ophthalmological device to the particular patient must have been made beforehand.

Since the range of motion of ophthalmological devices is restricted to approximately 30 mm on account of the limited height between the surface of the work table and the eye of the patient, the head of the patient is usually roughly positioned in advance, using the height adjustment of the chin rest. In addition, the distance from the chin rest to the forehead support must be correctly adjusted to the head size of the patient in order to achieve sufficient stability of the head.

The height adjustment of ±15 mm of the device is usually adequate to allow treatment of the vast majority of patients. However, for patients having head sizes in the borderline range, or also for children, additional corrections of the chin rest and of its distance from the forehead support are necessary. This cannot be omitted, since otherwise the eye may not be detectable under some circumstances, and an examination and/or treatment may not be possible. This is possible only after a subsequent correction, which results in disruption of the accustomed process, and thus, time delays and unnecessary waiting times.

However, assuming that the vertical distance between the bottom edge of the chin and the eye (canthus height) varies between 80 and 140 mm in patients, this results in a tolerance range of 60 mm. The tolerance range of 60 mm is much too large for fine positioning of ophthalmological devices in which the head of the patient is already resting on the chin support. Thus, there is a need for rough adjustment of the ophthalmological device to the particular patient, in particular, prior to fine positioning of the device.

As soon as an alignment of a patient with respect to a device via automatic movement is to be carried out, the question arises as to how possible collisions between the device and the patient may be avoided.

According to the prior art, in contrast to the above-described approaches concerning the fine adjustment of a ophthalmological device, rough positioning of the ophthalmological device to individual patients is not known. Instead, the rough alignment heretofore has generally been carried out manually, based on known patient data or by visual adjustment by the operator.

In this regard, U.S. Pat. No. 4,139,280 A describes a manual positioning aid for the positioning of patients with respect to the optical axis of an ophthalmological examination system, which is moved by purely mechanical means and which ensures maximum freedom of movement for the ophthalmologist. It is disadvantageous here that the operator must manually position the height of the eye of the patient.

The approach described in DE 198 16 486 A1 relates to a universal, modular examination system for examining human vision. To comfortably fix the head in a normal upright, relaxed posture, a modified head support composed of a chin rest and a forehead rest is used in combination with a functionally adapted seating device. The height-adjustable chair as well as the head support are mechanically adapted to the patient, so that the head of the patient cannot be turned during the examination and is kept still. Only in this way is it possible to ensure error-free examination results.

U.S. Pat. No. 6,309,068 B1 describes an automatic adjustment of a patient positioning aid, in which the ophthalmological system assesses whether the eye is already in the field of vision of the recording unit of the ophthalmological system when the head of the patient is present in the head support. By use of a control unit, the height of the chin rest is automatically adapted by application of a spring drive and a stopper lock. However, anatomically correct dimensions of facial features, which are necessary for correct positioning and the definition of safety distances and safety zones, are not detected.

However, the approaches known from the prior art have the disadvantage either that they are not suitable for the fine adjustment between the visual axis and the optical axis of the ophthalmological device, or that the rough positioning of the ophthalmological device to the eye of the patient is carried out manually, based on known patient data or by visual adjustment by the operator.

The known automated approach discloses no anatomically correct determination of facial dimensions, which are necessary for the rough positioning and definition of safety distances and safety zones.

LITERATURE

[1] Cristiano Niclass, Alexis Rochas, Pierre-Andre Besse, and Edoardo Charbon: "A CMOS 3D Camera with Millimetric Depth Resolution"; Swiss Federal Institute of Technology, Lausanne, Switzerland; AQUA-CONF 2004-001

[2] W.A.P. Smith and E. R. Hancock, Dept. of Computer Science, University of York; "Face Recognition using Shape-from-shading"; BMVC (13th British Machine Vision Conference) 2002; pages 597-606

[3] Holger Wagner, Axel Wiegmann, Richard Kowarschik, Friedrich Zöllner, Institute of Applied Optics, Friedrich-Schiller-University, Jena; "3D measurement of human face by stereophotogrammetry"; DGaO Proceedings 2005, ISSN: 1614-8436

SUMMARY OF THE INVENTION

The present invention includes an approach for the individual, automatic rough positioning of ophthalmological devices on a patient. It is the aim that the values determined for the rough positioning are also suitable for other ophthalmological devices, and are provided to same. The rough positioning is, according to an embodiment carried out before the patient sits down and places his head in a fixed position on the positioning aid. However, the rough positioning may also occur when the patient is already fixed in the patient positioning aid.

Using the proposed assembly for the automatic rough positioning of ophthalmological devices, having a positioning aid and a control unit for automatically aligning the visual axis of the eye with the optical axis of the ophthalmological device, this object is achieved in that the positioning aid for automatically aligning the visual axis of the eye with the optical axis of the ophthalmological device includes a chin rest and a forehead support which have appropriate controllable actuating devices, and that an additional measuring device for detecting the anatomically-to-scale three-dimensional geometry of the face of the patient is present, and is connected to the control unit of the ophthalmological device.

In the corresponding example method for the automatic rough adjustment of ophthalmological devices, an automatic alignment of the visual axis of the eye with the optical axis of the ophthalmological device is carried out using a positioning aid in the form of a chin rest and a forehead support, which have appropriate controllable actuating devices which are controlled by a control unit. In addition, a measuring device measures the three-dimensional geometry of the face of the patient anatomically to scale and relays this information to the control unit of the ophthalmological device, which, based on the detected geometry of the face of the patient, detects details such as the forehead, eyes, nose, and chin and determines the distances from eye to eye, from the vertex of the eye to the tip of the nose, and from the eye to the bottom edge of the chin, and on this basis establishes a safety zone for avoiding patient contact, and/or for the automatic rough adjustment generates appropriate actuating signals for the controllable actuating devices of the chin rest and the forehead support and transmits the signals to same.

The present approach is used for the individual, automatic rough positioning of ophthalmological devices for a patient to ensure the diagnostic or therapeutic treatment of the patient. The proposed approach may be used for a variety of devices in the field of ophthalmology.

BRIEF DESCRIPTION OF THE DRAWINGS

The invention is described in greater detail below with reference to exemplary embodiments, as follows.

DETAILED DESCRIPTION

The assembly according to the invention for the automatic rough adjustment of ophthalmological devices has a positioning aid and a control unit for automatically aligning the visual axis of the eye with the optical axis of the ophthalmological device, the positioning aid for automatically aligning the visual axis of the eye with the optical axis of the ophthalmological device being including a chin rest and a forehead support which have appropriate controllable actuating devices. The assembly has an additional measuring device for detecting the three-dimensional geometry of the face of the patient, the measuring device being connected to the control unit of the ophthalmological device.

In a first example variant of this assembly, the positioning aid includes a chin rest and a forehead support.

The detection of the three-dimensional geometry of the face of the patient includes the measurement of the complete three-dimensional shape of the face, i.e., the anatomically-to-scale shape and size of the face of the patient.

In a example variant of this assembly, the additional measuring device for detecting the three-dimensional geometry of the face of the patient is a 3D camera, which may contain various 3D measuring systems.

In this regard, it is important that the additional measuring device is not necessarily attached to the ophthalmological device; rather, it may also be situated separately from same. In addition to the spatial separation of the ophthalmological device and the measuring device, a temporal separation is also conceivable. Thus, the measuring device may be situated in the patient waiting room, for example.

The control unit of the ophthalmological device is able to detect details such as the forehead, eyes, nose, and chin based on the detected geometry of the face of the patient, and on this basis, to determine the required dimensions.

Figure 1A:
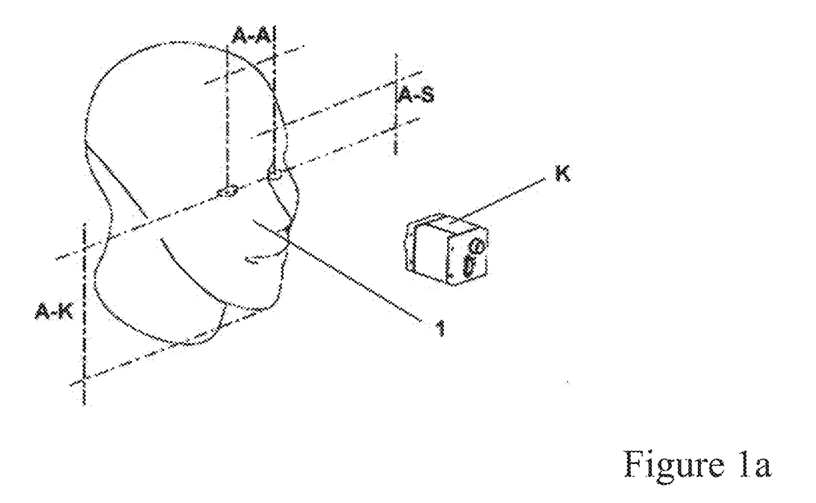
FIG. 1a: depicts distances in the x-y plane determined from the detected details of the geometry of the face of the patient.
Figure 1B:
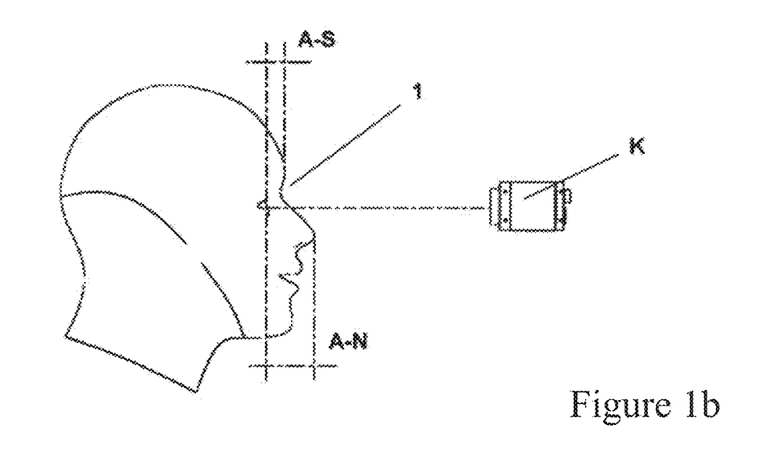
FIG. 1b: depicts these distances in the y-z plane.

In this regard, FIG. 1a and FIG. 1b show the required distances in the geometry of a face 1 of the patient detected by the 3D camera K; FIG. 1a shows the distances in the x-y plane determined from the detected details of the face 1 of the patient, and FIG. 1b shows these distances in the y-z plane. The distances required for an automatic rough adjustment are as follows:

Eye-eye (A-A),
Eye-forehead (A-S),
Eye-nose (A-N), and
Eye-chin (A-K).

It should be noted that the eye-forehead distance A-S in the x-y plane according to FIG. 1a describes the height, and in the y-z plane according to FIG. 1b describes the depth, of the distance between the eye and the forehead.

Based on the determined distances, the control unit of the ophthalmological device is thus able to establish safety distances and safety zones for automatically avoiding patient contact. It may thus be ensured that no patient collision can occur during the measurement operation using automatic positioning.

In addition, the control unit is able to generate appropriate actuating signals for the controllable actuating devices of the chin rest, forehead support, or measuring head, and to transmit the signals to same.

Actuating devices may include electric motors, pneumatic actuators, electromagnetic actuators, piezoelectric actuators, or other common actuators.

During the automatic alignment, automated motion occurs between the ophthalmological device and the patient. It is imperative to protect the patient from collision/contact with the device as the result of incorrect positioning.

Figure 2:
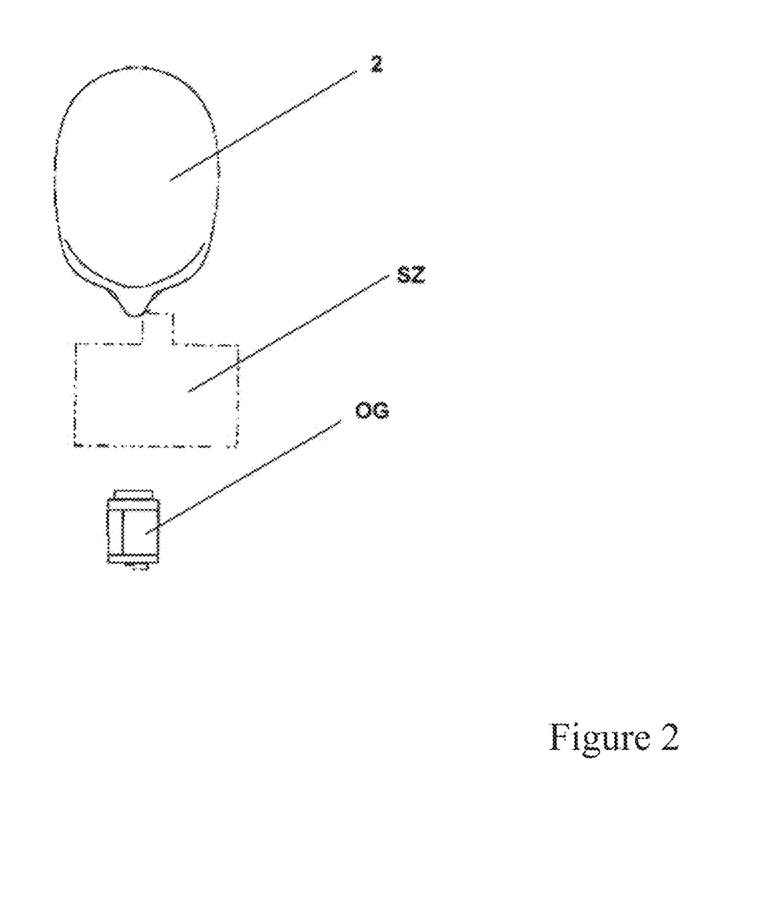
FIG. 2: depicts safety zones, computed based on the determined distances, for avoiding patient contact.

After the spatial detection of the topography of the face of the patient, the known system parameters of the ophthalmological system, such as travel distance, housing dimensions, and position and alignment of the patient positioning aid (forehead/chin rest) may be used to compute safety distances and a three-dimensional safety zone. The travel distance of the measuring head is limited corresponding to this safety zone, thus precluding a possible patient collision. In addition, before the patient leans on the head support or the forehead support the measuring head may be moved into a position which precludes a collision with the head of a patient from the very beginning In this regard, FIG. 2 shows safety zones SZ, computed based on the determined distances, for avoiding contact between the head 2 of the patient and the ophthalmological device OG. The safety zones computed from the corresponding facial dimensions are supplied to the ophthalmological device so that patient contact is avoided during adjustment of the ophthalmological device.

Based on the determined distances, the control unit generates appropriate actuating signals for the controllable actuating devices of the chin rest, forehead support, or measuring head, and transmits the signals to same.

In addition to the height of the chin rest, its distance from the forehead support is also roughly adjusted to the average adjustment range of the ophthalmological device. This ensures on the one hand that the ophthalmological device is able to use a preset "capture range," and on the other hand, that the overall range for the fine alignment may be smaller.

The chin rest or the forehead support is configured to the detected shape and size of the face of the patient, thus ensuring an automatic rough adjustment of the optical axis of the ophthalmological device to the visual axis of the particular patient.

During the determination of the required distances, the control unit of the ophthalmological device is able to detect extreme facial features, which for large irradiation or scanning angles could result in shadowing of measuring or treatment rays on the nose, eyelashes, eyebrows, and other body parts. This information may likewise be detected and stored. However, it is also possible to automatically correct presumed shadowing by the targeted tilting of the head of the patient in such a way that the measurements are facilitated.

In another example variant of the assembly according to the invention, the control unit of the ophthalmological device is also able to transmit the detected geometry of the face of the patient together with the determined required distances to a network, a database, computer-readable media, or other means, and thus provide same to other ophthalmological devices.

Ophthalmological devices which are not connected to one another via a network may provide the device with alignment data and/or the shape of the face for each patient via computer-readable data carriers, for example a patient card.

Accordingly, the detection of the geometry of the face of the patient together with the detection of details, the determination of required distances, the generation and transmission of appropriate actuating signals to the controllable actuating devices of the chin rest and the forehead support, and thus, the entire automatic rough adjustment in the x, y, and z directions, take place before the automatic fine alignment, and in particular before the patient places his head in the positioning aid.

In a final example variant of this assembly, the positioning aid is composed not only of a chin rest and a forehead support, but also includes a patient chair, an equipment table, or the like for the corresponding automatic rough adjustment.

In this regard, the assembly according to the invention for automatically aligning the visual axis of the eye with the optical axis of the ophthalmological device has a positioning aid and a control unit, the positioning aid for automatically aligning the visual axis of the eye with the optical axis of the ophthalmological device being composed of a patient chair and/or an equipment table which has/have appropriate controllable actuating device(s). The assembly has an additional measuring device for detecting the three-dimensional anatomically-to-scale geometry of the face and body of the patient, which is connected to the control unit of the ophthalmological device.

The control unit is able to detect details such as the chin, eye, buttocks, and knee based on the anatomically correctly measured geometry of the face and body of the patient, and on this basis to establish safety distances and safety zones for avoiding patient contact, and/or for the automatic alignment, to generate required actuating signals for the controllable actuating devices of the patient chair or patient table and transmit the signals to same. The control unit is also able to determine in an intermediate step, based on detected details, the distances required for a rough alignment.

Figure 4:
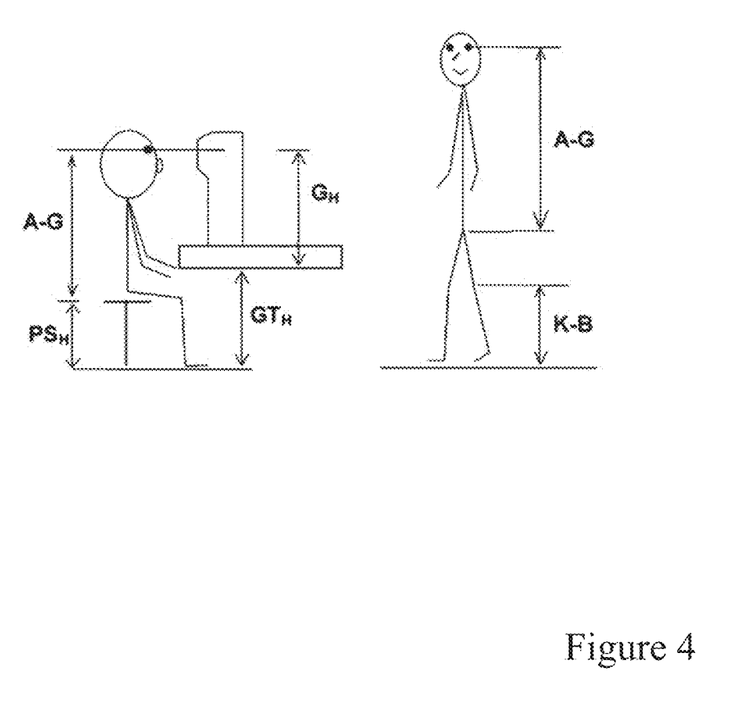
FIG. 4: depicts an overview, by way of example, of the dimensions determined based on the geometry of the face and the overall body structure of a patient, as well as dimensions computed from same which are necessary for avoiding patient contact and/or for the automatic rough adjustment.

In this regard, FIG. 4 shows an overview, by way of example, of the dimensions determined based on the geometry of the face and the overall body structure of a patient, as well as dimensions computed from same which are necessary for avoiding patient contact and/or for the automatic rough adjustment. Based on the detected details such as the eye, buttocks, and knee, the distance A-G from the eye to the buttocks and the distance K-B from the knee to the floor are determined from the 3D measurement, which in turn form the basis for computing the dimensions for the height of the patient chair $PS_H$ and the height of the equipment table $GT_H$, the height of the device $G_H$ being specified.

As is apparent from FIG. 4, the known and measured dimensions may be used to set the optimal chair height and equipment table height for the particular patient. The height of the patient chair $PS_H$ and of the equipment table $GT_H$ may be used to check the safety zone for protecting the knee from pinching.

In the method according to the invention for the automatic rough adjustment of ophthalmological devices, an automatic alignment of the visual axis of the eye with the optical axis of the ophthalmological device is carried out by application of a positioning aid in the form of a chin rest and a forehead support which have appropriate actuating devices which are controlled by a control unit. In addition, a measuring device detects the three-dimensional geometry of the face of the patient and relays this information to the control unit of the ophthalmological device. Based on the geometry of the face of the patient which is measured true to geometric scale, the control unit detects details such as the forehead, eyes, nose, and chin, determines the eye-eye, eye-forehead, eye-nose, and eye-chin distances, and on this basis establishes safety zones for avoiding patient contact, and/or for the automatic rough adjustment generates appropriate actuating signals for the controllable actuating devices of the chin rest and the forehead support and transmits the signals to same.

An automatic alignment of the visual axis and the optical axis occurs by application of the positioning aid composed of a chin rest and a forehead support.

The detection of the three-dimensional geometry of the face of the patient includes the determination of the complete, three-dimensional shape of the face, i.e., the shape and size of the face of the patient. The three-dimensional geometry of the face of the patient is may be detected by 3D measurement in anatomically correct absolute values.

In a first example embodiment of the method, the 3D measurement is recorded using a 3D camera in the "time of flight" method.

In the "time of flight" (TOF) method of a 3D camera, the distances are determined by measuring the propagation time of the light. For this purpose, the scene is illuminated from the front by a light pulse. For each pixel, the camera measures the time required for the light to reach the object and return. The required time is directly proportional to the distance. Thus, for each pixel the camera supplies the distance from the object imaged thereon. The principle corresponds to laser scanning, with the advantage that an entire scene is recorded at once, and does not have to be scanned. In this regard, Cristiano Niclass et al. describe the use of a TOF camera for facial recognition in literature reference [1].

In a second example embodiment of the method, the 3D measurement is made using a 3D camera in the "shape from shading" method.

In contrast to the TOF method, in the "shape from shading" method the object is preferably illuminated by different illumination sources situated at the side or also in front, wherein the angle of incidence of the illumination source must be known. The surface of the object is then detected by analyzing the brightness distribution of the reflected illumination sources. For this purpose, these illumination sources may emit uniform light as well as structured light, which may be spatially and temporally defined in an intermittent manner. Facial recognition by the "shape from shading" method is discussed in greater detail by W. A. P. Smith and E. R. Hancock in literature reference [2].

In a third example embodiment, the 3D measurement for detecting the geometry of the face of the patient is carried out by stereophotogrammetry, using an assembly composed of two cameras. Stereophotogrammetry is an image measuring method in which the object is recorded from two different positions in order to reconstruct the spatial position and precise three-dimensional shape of the object. The use of stereophotogrammetry for facial recognition is discussed in greater detail by H. Wagner et al. in literature reference [3].

In this regard, it is essential to the invention that the 3D measurement for detecting the geometry of the face of the patient may be recorded temporally and/or spatially independently from the ophthalmological device. Thus, for example, it may be advantageous for the measurement to take place during patient check-in or in the patient waiting room.

It is also essential to the invention that the 3D measurement for detecting the geometry of the face of the patient preferably takes place before the automatic fine alignment of the two axes is carried out, and in particular also before the patient has placed his head in the patient positioning aid.

After the geometry of the face of the patient is detected by a 3D measurement, in a next method step the control unit determines details of the face of the patient such as the forehead, eyes, nose, and chin, and determines the eye-eye, eye-forehead, eye-nose, and eye-chin distances.

Based on the determined distances, in a further method step the control unit establishes safety distances and safety zones for avoiding patient contact, and/or for the automatic rough adjustment generates appropriate actuating signals for the controllable actuating devices of the chin rest and the forehead support and transmits the signals to same. The safety distances and safety zones computed from the corresponding facial dimensions are provided to the ophthalmological device, thus avoiding patient contact during adjustment of the ophthalmological device.

Based on the actuating signals for the controllable actuating devices which are generated and transmitted by the control unit, the height of the chin rest and its distance from the forehead support are roughly adjusted to the average adjustment range of the ophthalmological device. This ensures on the one hand that the ophthalmological device is able to use a "capture range" that is preset for the fine alignment, and on the other hand, that the overall range for the fine alignment is reduced.

Electric motors, pneumatic actuators, electromagnetic actuators, piezoelectric actuators, or other common actuators may be used as actuating devices.

Figure 3:
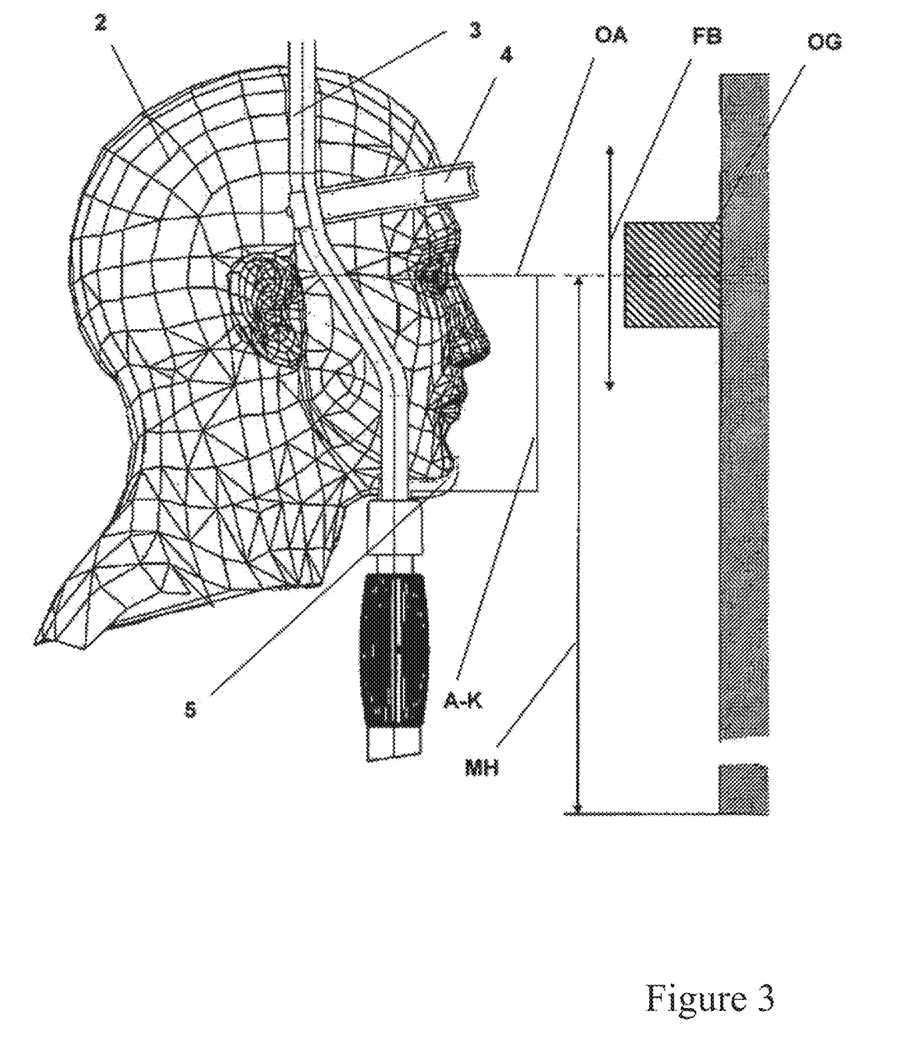
FIG. 3: depicts a head of a patient fixed to the positioning aid of an ophthalmological device.

FIG. 3 depicts a head of a patient fixed to the positioning aid of an ophthalmological device. The positioning aid 3 of an ophthalmological device OG (not illustrated in greater detail) is composed of a chin rest 5 and a forehead support 4. The head 2 of the patient is securely fixed by placing the chin on the chin rest 5 and leaning the forehead on the forehead support 4. FIG. 3 also depicts the eye-chin distance A-K required for the rough alignment, as well as the optical axis OA, indicated by a dashed-dotted line, of the ophthalmological device OG. The arrow MH indicates the average height of the optical axis OA, while the double arrow FB represents the capture range of the ophthalmological device OG for the subsequent fine alignment.

The chin rest or the forehead support is set to the detected shape and size of the face of the patient, thus ensuring an automatic rough adjustment of the optical axis of the ophthalmological device to the visual axis of the particular patient. Of course, in addition to a chin rest and a forehead support, the automatic rough adjustment may also involve a patient chair, a patient couch, or the like.

In another example embodiment of the method, during the determination of the required distances the control unit of the ophthalmological device may detect extreme facial features, which for large irradiation or scanning angles could result in shadowing of measuring or treatment rays on the nose, eyelashes, eyebrows, and other body parts. This information may likewise be detected and stored. However, it is also possible to automatically correct presumed shadowing by the targeted tilting of the head of the patient in such a way that the measurements are facilitated.

In a next example embodiment of the method according to the invention, the detected geometry of the face of the patient together with the determined eye-eye, eye-forehead, eye-nose, and eye-chin distances are transmitted to a network, a database, computer-readable media, or other means, and thus provided to other ophthalmological devices.

Ophthalmological devices which are not connected to one another via a network may provide the device with the alignment data and/or the shape of the face for each patient via computer-readable data carriers, for example a patient card.

Accordingly, the detection of the geometry of the face of the patient together with the detection of details, the determination of required distances, the generation and transmission of appropriate actuating signals to the controllable actuating devices of the chin rest and the forehead support, and thus, the entire automatic rough adjustment in the x, y, and z directions, take place before the automatic fine alignment, and in particular before the patient places his head in the positioning aid.

In a final example embodiment of the method according to the invention, the automatic alignment of the visual axis and the optical axis is carried out by application of the positioning aid, which in addition to a chin rest and a forehead support also includes a patient chair, an equipment table, or the like.

In this regard, the automatic alignment of the visual axis of the eye with the optical axis of the ophthalmological device is carried out by application of a positioning aid in the form of a patient chair and/or equipment table which has/have appropriate actuating unit(s) which are controlled by a control unit. A measuring device measures the three-dimensional geometry of the face and body of the patient anatomically to scale and relays this information to the control unit of the ophthalmological device. Based on the geometry of the face and body of the patient measured anatomically to scale, the control unit detects details such as the chin, eye, buttocks, and knee, and on this basis establishes safety distances and safety zones for avoiding patient contact, and/or for the automatic alignment generates appropriate actuating signals for the controllable actuating devices of the patient chair or patient table and transmits the signals to same.

For this purpose, a 3D detection of the geometry of the face and of the overall body structure of a patient is carried out, for example to use same for presetting the height of the patient chair. Heretofore, the setting for each measurement has been made manually by the medical practitioner, which is time-consuming. The setting is made by questioning the patient about his subjective seating comfort, and is therefore imprecise. However, a good sitting position influences the posture of the head in the head support and the behavior of the patient during the measurement. An optimal sitting posture also affects the drift movements, and thus the measuring results. Measurements are preferentially carried out right away, which shortens the treatment time.

As described above, based on the anatomically correctly measured geometry of the face and body of the patient the control unit detects details such as the chin, eye, buttocks, and knee, in an intermediate step determines the distances required for a rough alignment, and for the automatic alignment generates appropriate actuating signals for the controllable actuating devices of the patient chair or equipment table and transmits the signals to same.

In this regard, FIG. 4 shows an overview, by way of example, of the dimensions determined based on the geometry of the face and the overall body structure of a patient, as well as dimensions computed from same which are necessary for avoiding patient contact and/or for the automatic rough adjustment. Based on the detected details such as the eye, buttocks, and knee, the distance A-G from the eye to the buttocks and the distance K-B from the knee to the floor may be determined from the 3D measurement, which in turn form the basis for computing the dimensions for the height of the patient chair $PS_H$ and the height of the equipment table $GT_H$, the height of the device $G_H$ being predefined.

As is apparent from FIG. 4, the known and measured dimensions may be used to set the optimal chair height and equipment table height for the particular patient. The height of the patient chair $PS_H$ and of the equipment table $GT_H$ may be used to check the safety zone for protecting the knee from pinching.

According to the invention, the patient is measured before the actual measurement and before he is situated in the patient positioning aid, so that at the time of the actual ophthalmological measurement the patient positioning aid has already been automatically prepositioned, and the device has computed the safety zone for travel distances.

Such data, together with the patient data, are also may be stored locally on the device, or for globally availability, on patient data cards (memory media such as the known chip card for patients), so that optimal presetting may be ensured within a very short time.

This procedure reduces the level of effort for data entry and manual alignment, and decreases the total diagnostic time, thus increasing the patient throughput rate with the medical practitioner.

By use of the assembly according to the invention and the corresponding method, an approach is provided by application of which an automatic rough positioning of ophthalmological devices on a patient is possible to be able to ensure the diagnostic or therapeutic treatment of the patient.

The values determined for the rough positioning are also suitable for other ophthalmological devices, and are provided to same.

Since the rough positioning is carried out before the patient has sat down and placed his head in a fixed position on the positioning aid, patient injuries are avoided.

The proposed approach allows the capture range for the fine alignment of the device to be reduced to ±15 mm, according to another embodiment to ±7.5 mm, and according to another embodiment to ±5 mm. In return, this means a possible increase in the motion resolution for a measuring head motion, and in particular also a reduction in the overall device height, since the total range of motion no longer has to be covered by the device head motion, and instead the anatomic variations in the patients are already covered by the position of the patient positioning aid.

Using the assembly according to the invention and the corresponding method, in essence the workflow in setting up ophthalmological devices on the particular patient before his diagnostic and/or therapeutic treatment may be optimized, and safety may be improved.

The invention claimed is:

1. An assembly for automatic rough positioning of ophthalmological devices, comprising:
   a positioning aid; and
   a control unit operably coupled to the positioning aid that automatically aligns the visual axis of the eye with the optical axis of the ophthalmological device;
   wherein the positioning aid that automatically aligns the visual axis of the eye with the optical axis of the ophthalmological device includes a chin rest and a forehead support operably coupled to appropriate controllable actuating devices; and
   further comprising an additional measuring device that is operably connected to the control unit of the ophthalmological device and wherein the additional measuring device includes a three dimensional camera that captures three dimensional image data of a face of a patient;

wherein the control unit calculates anatomically-to-scale three-dimensional geometry of the face of a patient from the three dimensional image data including dimensions of the face in a first plane and in a second plane orthogonal to the first plane.

2. The assembly according to claim 1, wherein the additional measuring device that detects the three-dimensional geometry of the face of the patient comprises an assembly having two cameras.

3. The assembly according to claim 1, wherein the additional measuring device is attached to the ophthalmological device.

4. The assembly according to claim 1, wherein the additional measuring device is situated separately from the ophthalmological device.

5. The assembly according to claim 1, wherein the control unit of the ophthalmological device together with additional measuring device detect details of the face of the patient based on the detected geometry and to measure at least one of the distances eye-eye, eye-nose, eye-forehead, and eye-chin anatomically to scale.

6. The assembly according to claim 1, wherein the details of the face detected are selected from a group consisting of the forehead, eyes, nose, and chin.

7. The assembly according to claim 5, wherein based on the determined distances, the control unit of the ophthalmological device establish safety zones for automatically avoiding patient contact.

8. The assembly according to claim 5, wherein based on the determined distances, for the automatic rough adjustment, the control unit generates appropriate actuating signals for controllable actuating devices of the chin rest, the forehead support, or a measuring head, and transmits the signals to the chin rest, the forehead support, or the measuring head.

9. The assembly according to claim 1, wherein the control unit of the ophthalmological device transmits the geometry of the face of the patient measured anatomically to scale together with determined distances to a network, a database or computer-readable media and thus provides the geometry of the face of the patient measured anatomically to scale together with the determined distances to other ophthalmological devices.

10. An assembly for the automatic rough positioning of ophthalmological devices, comprising:
a positioning aid operably coupled to a control unit that automatically aligns a visual axis of the eye with an optical axis of the ophthalmological device;
wherein the positioning aid that automatically aligns the visual axis of the eye with the optical axis of the ophthalmological device includes a patient chair and/or an equipment table having appropriate controllable actuating devices, and an additional measuring device for detecting three-dimensional anatomically-to-scale geometry of a face and body of the patient; and
the additional measuring device is operably connected to the control unit of the ophthalmological device and includes a three dimensional camera that captures three dimensional image data of a face of a patient; and
wherein the control unit determines from the three dimensional image data dimensions of the face of the patient in a first plane and in a second plane orthogonal to the first plane.

11. A method for automatic rough positioning of an ophthalmological device, comprising:
carrying out an automatic alignment of the visual axis of the eye with the optical axis of the ophthalmological device by application of a positioning aid in the form of a chin rest and a forehead support which have appropriate actuating devices and which are controlled by a control unit;
measuring three-dimensional geometry of the face of the patient anatomically to scale by application of a measuring device that is operably connected to the control unit and wherein the additional measuring device includes a three dimensional camera;
capturing three dimensional image data of a face of a patient;
relaying information related to the three-dimensional geometry of the face of the patient to the control unit of the ophthalmological device;
detecting details of the face of the patient based on the geometry of the face of the patient based on the three dimensional image data, the details including at least one of a forehead, eyes, a nose, and a chin; and
determining at least one of distances eye-eye, eye-forehead, eye-nose, and eye-chin in at least one plane based on the three dimensional image data, and
performing at least one of, establishing safety zones for avoiding patient contact or, for the automatic alignment, generating appropriate actuating signals for the controllable actuating devices of the chin rest, the forehead support, or measuring head, and
transmitting the signals to the chin rest, forehead support, or measuring head.

12. The method according to claim 11, further comprising determining the three-dimensional geometry of the face of the patient in anatomically-to-scale absolute values by application of 3D measurement.

13. The method according to claim 11, further comprising detecting the three-dimensional geometry of the face of the patient using the 3D camera in the "time of flight" method, or using a standard camera in the "shape from shading" method.

14. The method according to claim 11, further comprising detecting the three-dimensional geometry of the face of the patient by stereophotogrammetry, using an assembly having two cameras.

15. The method according to claim 11, further comprising detecting the three-dimensional geometry of the face of the patient temporally and/or spatially independently from the ophthalmological device.

16. The method according to claim 11, further comprising detecting the three-dimensional geometry of the face of the patient before the automatic alignment of the visual axis of the eye with the optical axis of the ophthalmological device is carried out.

17. The method according to claim 11, further comprising detecting the three-dimensional geometry of the face of the patient before the patient places his head in the patient positioning aid.

18. The method according to claim 11, further comprising storing the detected geometry of the face of the patient together with the determined distances on a network, a database or computer-readable media and, thus, providing the detected geometry of the face of the patient together with the determined distances to other ophthalmological devices.

19. A method for the automatic rough positioning of ophthalmological devices, comprising:
carrying out an automatic alignment of the visual axis of the eye with the optical axis of the ophthalmological device by application of a positioning aid in the form of a patient chair and/or equipment table having appropriate actuating units which are controlled by a control unit;

measuring three-dimensional geometry of a face and a body of the patient anatomically to scale by capturing three dimensional image data with a three dimensional camera;

relaying information on the three-dimensional geometry of a face and a body of the patient determined from the three dimensional image data to a control unit of the ophthalmological device;

detecting, based on the three dimensional image data and on the geometry of the face and body of the patient measured anatomically to scale, details selected from a group consisting of a chin, at least one eye, buttocks and a knee, and performing at least one of, establishing safety zones for avoiding patient contact with a measuring head of the ophthalmological device or for the automatic alignment, generating appropriate actuating signals for the controllable actuating devices of the patient chair or patient table, and transmitting the signals to the controllable actuating devices of the patient chair or patient table.

* * * * *